(12) United States Patent
Ingle et al.

(10) Patent No.: US 6,679,256 B2
(45) Date of Patent: Jan. 20, 2004

(54) SYSTEMS AND METHODS FOR EXTRACTING POWDERS FROM RECEPTACLES

(75) Inventors: Frank W. Ingle, Palo Alto, CA (US); Steve Paboojian, Menlo Park, CA (US); Carlos Schuler, Cupertino, CA (US); Andrew Clark, Half Moon Bay, CA (US)

(73) Assignee: Nektar Therapeutics, San Carlos, CA (US)

(*) Notice: Subject to any disclaimer, the term of this patent is extended or adjusted under 35 U.S.C. 154(b) by 360 days.

(21) Appl. No.: 09/731,368

(22) Filed: Dec. 6, 2000

(65) Prior Publication Data

US 2001/0029948 A1 Oct. 18, 2001

Related U.S. Application Data

(60) Provisional application No. 60/172,317, filed on Dec. 17, 1999.

(51) Int. Cl.$^7$ .................... A61M 15/00; A61M 16/00
(52) U.S. Cl. ..................... 128/203.21; 128/203.12; 128/203.15; 604/58
(58) Field of Search .............. 1258/203.15, 203.12, 1258/203.17, 203.26, 203.27, 206.28, 204.25, 204.24, 203.21; 604/58; 220/708, 709

(56) References Cited

U.S. PATENT DOCUMENTS

| 478,744 | A | 7/1892 | Evans |
| 513,189 | A | 1/1894 | Knode |

(List continued on next page.)

FOREIGN PATENT DOCUMENTS

| AU | 20384/92 | 2/1993 |
| EP | 0 129 985 B1 | 1/1985 |
| EP | 0347779 A2 | 12/1989 |
| EP | 0 473 965 A1 | 8/1991 |
| EP | 0467172 B1 | 1/1992 |
| EP | 0468914 A1 | 1/1992 |
| EP | 0490797 A1 | 6/1992 |
| NL | 7712041 | 3/1979 |
| SU | 0628930 | 9/1978 |
| SU | 1003926 | 3/1983 |
| WO | WO 89/07464 | 8/1989 |
| WO | WO 90/07351 | 7/1990 |
| WO | WO 91/02558 | 3/1991 |
| WO | WO 92/20391 | 11/1992 |
| WO | WO 93/09832 | 5/1993 |
| WO | WO 94/03225 | 2/1994 |
| WO | WO 94/06498 | 3/1994 |
| WO | WO 94/08552 | 4/1994 |
| WO | WO 95/06491 | 3/1995 |

OTHER PUBLICATIONS

G. K., Budrick et al., *Chemical and Petroleum Engineering*, vol. 14, Nos. 9–10, Sep.–Oct. 1978.

V.M. Zholob et al. Translated from *Poroshkovvaya Metallurgya*, 1979, No. 6 (198), pp. 13–16.

Chemical Engineers' Handbook. Fifth Edition. Prepared under editorial direction of Robert H. Perry. Ejectors. pp. 6–29 through 6–32.

(List continued on next page.)

*Primary Examiner*—Weilun Lo
*Assistant Examiner*—Michael G. Mendoza
(74) *Attorney, Agent, or Firm*—Guy Tucker; Felissa H. Cagan

(57) ABSTRACT

A method for aerosolizing a powder utilizes a receptacle having a cavity containing a powder. An access end of an extraction tube is inserted into the cavity, and an inlet opening is formed in the receptacle. A pressurized gas is flowed through the inlet opening, through the cavity and through the extraction tube to move the powder in the cavity into the extraction tube where the powder is entrained in the gas to form an aerosol.

28 Claims, 4 Drawing Sheets

U.S. PATENT DOCUMENTS

| | | | |
|---|---|---|---|
| 2,533,065 | A | 12/1950 | Taplin et al. |
| 2,549,303 | A | 4/1951 | Friden |
| 2,570,774 | A | 10/1951 | Davis |
| 2,603,216 | A | 7/1952 | Taplin |
| 3,425,600 | A | 2/1969 | Abplanalp |
| 3,809,084 | A * | 5/1974 | Hansen ................ 128/203.15 |
| 3,918,451 | A | 11/1975 | Steil |
| 3,921,637 | A | 11/1975 | Bennie et al. |
| 3,967,761 | A | 7/1976 | Melton, Jr. et al. |
| 3,991,761 | A | 11/1976 | Cocozza |
| 3,994,421 | A | 11/1976 | Hansen |
| 4,018,185 | A | 4/1977 | Myers |
| 4,069,819 | A | 1/1978 | Valentini et al. |
| 4,105,027 | A | 8/1978 | Lundquist |
| 4,114,615 | A | 9/1978 | Wetterlin |
| 4,249,526 | A | 2/1981 | Dean et al. |
| 4,338,931 | A | 7/1982 | Cavazza |
| 4,446,862 | A | 5/1984 | Baum et al. |
| 4,548,524 | A * | 10/1985 | Seager ................... 222/205 |
| 4,570,630 | A | 2/1986 | Elliott et al. |
| 4,627,432 | A | 12/1986 | Newell et al. |
| 4,668,218 | A | 5/1987 | Virtanen |
| 4,778,054 | A | 10/1988 | Newell et al. |
| 4,807,814 | A | 2/1989 | Douche et al. |
| 4,811,731 | A | 3/1989 | Newell et al. |
| 4,860,740 | A | 8/1989 | Kirk et al. |
| 4,884,565 | A | 12/1989 | Cocozza |
| 4,889,114 | A | 12/1989 | Kladders |
| 4,984,158 | A | 1/1991 | Hillsman |
| 4,995,385 | A | 2/1991 | Valentini et al. |
| 5,035,237 | A | 7/1991 | Newell et al. |
| 5,048,514 | A | 9/1991 | Ramella |
| 5,186,166 | A | 2/1993 | Riggs et al. |
| 5,201,308 | A | 4/1993 | Newhouse |
| 5,207,217 | A | 5/1993 | Cocozza et al. |
| 5,287,850 | A | 2/1994 | Haber et al. |
| 5,320,714 | A | 6/1994 | Brendel |
| 5,337,740 | A | 8/1994 | Armstrong et al. |
| 5,349,947 | A | 9/1994 | Newhouse et al. |
| 5,355,872 | A | 10/1994 | Riggs et al. |
| 5,366,122 | A | 11/1994 | Guentert et al. |
| 5,388,572 | A | 2/1995 | Mulhauser et al. |
| 5,458,135 | A | 10/1995 | Patton et al. |
| 5,505,193 | A * | 4/1996 | Ballini et al. .......... 128/200.14 |
| 5,505,194 | A | 4/1996 | Adjei et al. |
| 5,533,502 | A | 7/1996 | Piper |
| 5,619,985 | A * | 4/1997 | Ohki et al. ............ 128/203.15 |
| 5,740,794 | A | 4/1998 | Smith et al. |
| 5,775,320 | A | 7/1998 | Patton et al. |
| 5,785,049 | A | 7/1998 | Smith et al. |
| 5,875,776 | A * | 3/1999 | Vaghefi ................. 128/203.12 |
| 5,884,621 | A * | 3/1999 | Matsugi et al. ........ 128/203.15 |
| 5,921,236 | A * | 7/1999 | Ohki et al. ............ 128/203.12 |
| 6,089,228 | A | 7/2000 | Smith et al. |
| 6,105,574 | A * | 8/2000 | Jahnsson ............... 128/203.15 |
| 6,257,233 | B1 * | 7/2001 | Burr et al. ............. 128/203.15 |

OTHER PUBLICATIONS

C.L. Witham et al., Workshop on Dissemination Techniques.

M. Bohnet, *Powder Technology*, 1984, pp. 302–313.

L.S. Fox et al., *Power and Bulk Engineering*, 1988. pp. 33–36.

A.N. Pittman et al., Solids Handling Conference, 1989. Paper 34, pp. C41–C51.

P.R. Byron et al., *Journal of Aerosol Medicine*, 1994, vol. 7, No. 1, pp. 49–75.

* cited by examiner

SYSTEMS AND METHODS FOR EXTRACTING POWDERS FROM RECEPTACLES

CROSS REFERENCE TO RELATED APPLICATIONS

This application is a continuation in part application and claims the benefit of U.S. Provisional Patent Application No. 60/172,317, filed Dec. 17, 1999, the complete disclosure of which is herein incorporated by reference.

BACKGROUND OF THE INVENTION

This invention relates generally to the field of drug delivery, and in particular to the pulmonary delivery of powdered medicaments. More specifically, the invention relates to techniques for extracting powdered medicaments from receptacles during the aerosolizing process.

One promising way to deliver various drugs to a patient is by pulmonary delivery where a drug dispersion or aerosol is inhaled by the patient to permit the active drug within the dispersion to reach the distal or alveolar regions of the lung. Pulmonary drug delivery has shown to be particularly promising because certain drugs have been found to readily absorb within the blood circulation. For example, pulmonary delivery may be a useful approach for proteins and polypeptides that are difficult to deliver by other routes of administration.

A variety of techniques have been employed to deliver drugs to the lungs including liquid nebulizers, metered dose inhalers, and the like. Of particular interest to the invention are dry powder dispersion devices that are able to aerosolize powdered medicaments for inhalation by the patient. Exemplary apparatus for aerosolizing powdered medicaments are described in U.S. Pat. Nos. 5,458,135, 5,775,320, 5,740,794, 5,785,049, and 6,089,228, and copending U.S. patent application Ser. No. 09/312,434, filed Jun. 4, 1999, Ser. No. 60/136,518, filed May 28, 1999, Ser. No. 60/141,793, filed Jun. 30, 1999, and Ser. No. 09/583,312, filed May 30, 2000, the complete disclosures of which are herein incorporated by reference.

At least some of the apparatus described in the above references utilize a high pressure gas stream to draw the powder into an extraction tube where the powder is deagglomerated, entrained in the high pressure gas stream, and exits as an aerosol suitable for inhalation. In some cases, such apparatus may utilize a receptacle that has a penetrable lid. The extraction tube is inserted through the lid and a vent is also formed in the lid. The high pressure gas stream then draws air through the receptacle and into the extraction tube. The air drawn through the receptacle extracts the powder where it joins with the high pressure gas stream to form the aerosol. The powder is deagglomerated by the high shear forces in the gas flow.

This invention is related to alternative ways to extract powder from receptacles that store the powder.

SUMMARY OF THE INVENTION

The invention provides apparatus and methods for aerosolizing powders for subsequent inhalation. Such powders may conveniently be sealed within a cavity of a receptacle until ready for aerosolization. According to one method, an access end of an extraction tube is inserted into the cavity, and an inlet opening is also formed in the receptacle. A pressurized gas at high velocity is flowed through the inlet opening, through the cavity and through the extraction tube to move the powder in the cavity into the extraction tube where the powder is entrained in the gas to form an aerosol. The high velocity gas stream assists in scouring sides of the cavity in order to facilitate removal of the powder. The high velocity gas stream also produces a mechanical impulse against the walls of the receptacle, freeing the film of powder with a "flick".

In one aspect, a seal is produced between the receptacle and the extraction tube. By permitting the pressurized gas to enter the cavity only through the inlet opening, substantially all of the entering gas flows into the extraction tube along with the powder within the cavity. In some cases, multiple inlet openings may be formed to permit the pressurized gas to flow into the cavity from multiple locations. In a similar manner, multiple outlet tubes may be inserted into the cavity to extract the powder from multiple locations. In a further aspect, the gas may be pressurized to a pressure in the range from about 1 psi to about 300 psi.

In another aspect, the inlet opening may be formed by piercing the receptacle with an access end of an inlet tube. In this way, the pressurized gas may be flowed through the inlet tube and into the cavity. Conveniently, the pressurized gas may be stored within a container. In this manner, the pressurized gas may be released from the container to permit the pressurized gas to flow through the inlet opening. In one aspect, the container may comprise a cylinder, and a piston may be moved within the cylinder to produce the pressurized gas. Alternatively, the gas source may be a liquefied gas which is introduced into the receptacle where it vaporizes. In one particular aspect, the aerosol may be captured in a capture chamber where it may be inhaled by a patient.

In another embodiment, the inlet opening is formed in the bottom of the cavity such that the hole is generally aligned with the access end of the extraction tube. A pressurized gas is then flowed through the inlet opening in the bottom end of the receptacle and then through the extraction tube to move the powder in the cavity into the extraction tube where the powder is entrained in the gas to form an aerosol. Optionally, the receptacle may be configured as described in copending U.S. application Ser. Nos. 60/172,317, filed Dec. 17, 1999 and 09/731,318, filed on the same date as the present application, the disclosure of which is herein incorporated by reference. For example, the receptacle may include a raised central region that extends upwardly into the cavity and is generally aligned with the extraction tube.

The invention further provides an apparatus for aerosolizing a powdered medicament. The apparatus comprises a housing for holding a receptacle having a cavity that holds a powder. A hole is provided in the housing to form an inlet hole in the receptacle. Further, at least one extraction tube is provided for placement into the cavity. The apparatus further includes a pressure source to provide a pressurized gas into the cavity through the inlet hole to permit the pressurized gas to flow through the cavity at a relatively high velocity and then through the extraction tube. In so doing, the pressurized gas moves the powder in the cavity into the extraction tube where the powder is entrained in the gas and deagglomerated by the large shear forces to form an aerosol.

In one aspect, the hole forming mechanism comprises at least one inlet tube having an access end that is adapted to pierce the receptacle. Further, the pressure source is coupled to the inlet tube. Seals may be formed between the receptacle and the inlet and extraction tubes so that gases may only enter into the cavity through the inlet tube and may exit only through the extraction tube.

In another aspect, the pressure source comprises a cylinder, and a piston that is slidable within the cylinder. A valve is utilized to release the pressurized gas from the cylinder. The pressurized gas may be at a pressure in the range from about 1 psi to about 300 psi.

In yet another aspect, the extraction tube may have an access end that is adapted to pierce the receptacle. Further, a capture chamber may be coupled to the housing to receive the aerosol. The capture chamber may include a mouthpiece to permit the aerosol to be inhaled. In one aspect, the capture chamber may include a vent with flap valve to permit gases to enter into the capture chamber as the aerosol is inhaled.

In another embodiment, the housing may include a holder for holding the receptacle. The piercing mechanism may be configured to pierce an inlet opening in a bottom end of the receptacle. With this configuration, the extraction tube may be placed into the cavity so as to be spaced above the bottom end of the receptacle and to be aligned with the opening in the bottom end. In this way, the pressurized gas may flow through the inlet opening in the bottom end of the receptacle and into the extraction tube to move the powder from the cavity and into the extraction tube where the powder is entrained in the gas to form an aerosol.

DESCRIPTION OF THE SPECIFIC EMBODIMENTS

Figure 1:
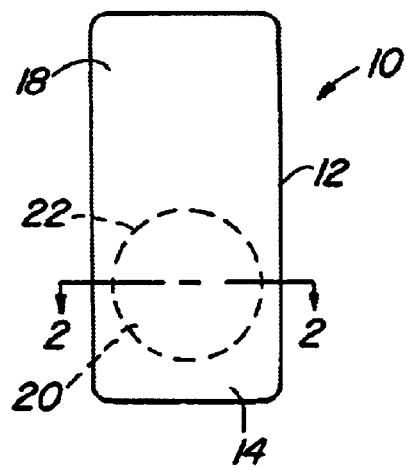
FIG. 1 is a top view of one embodiment of a receptacle for holding a powder according to the invention.

The invention provides exemplary techniques and equipment for extracting powder that is held within a receptacle, typically within a sealed cavity. In one aspect, the powder extracted is entrained in a high pressure gas stream to aerosolize the powder so that it will be suitable for inhalation by a patient. The invention may be utilized with essentially any type of receptacle within which the powder is sealed. Merely by way of example, one type of receptacle that may be utilized with the invention are widely available "blister packs". Examples of other types of receptacles are described in U.S. Pat. No. 5,740,794 and co-pending U.S. application Ser. No. 09/731,318, filed on the same date as the present application, previously incorporated by reference. However, it will be appreciated that the invention is not intended to be limited to these specific types of receptacles.

The powders of the invention may be extracted by creating an opening or access way into the receptacle and introducing a pressurized gas, such as air, into the receptacle at a relatively high velocity. The high pressure gas is used to "blast" the powder loose and then remove the loosened powder from the cavity through the access way. Such a technique is particularly useful in reducing the amount of material remaining within the cavity, including any remaining loose powder, chunks of powder, and/or films of powder. In this way, the amount of powder available for inhalation is increased. Further, such techniques insure a more consistent dosage each time an aerosolization device is operated. Also, the action of the high pressure blast has been demonstrated to produce a low average particle size, indicating successful deagglomeration.

The pressurized gas that is introduced into the cavity is used to both reduce the boundary layer of fluid flow at the surface of the cavity until it is smaller than the particle size and to propel particles at a high velocity so that they impact the cavity surface. In this way, the cavity surface is scoured to remove any powder. The pressurized gas is preferably introduced into the cavity at a relatively high velocity and low volume so that it dissipates most of its energy within the receptacle. To produce such a high gas flow, a source of pressured gas may be employed. The plumbing between the gas source and the cavity is preferably configured such that the volume available for expansion and the flow resistance are minimized. In this way, energy losses experienced when transferring the gas from the source to the cavity are minimized. By maintaining the gas at a high energy level, a low volume, high velocity gas flow is produced within the cavity to more effectively scour the powder from the cavity. In this way, less powder is left in the cavity, even when the receptacle has been exposed to harsh shipping conditions which normally tends to compact it into a thick film of powder.

Merely by way of example, when used with powders having a mean size in the range from about 0.5 $\mu$m to about 10 $\mu$m, and more preferably from about 0.5 $\mu$m to about 5 $\mu$m, that are stored within a cavity having a volume sufficient to hold up to about 50 mgs of powder, the gas stream may be at a pressure within the range from about 1 psi to about 300 psi when entering the cavity. Further, the volume of the gas may be in the range from about 1 $cm^3$ to about 20 $cm^3$ (STP).

A variety of techniques may be employed to create the high pressure gas stream to cause the air to be drawn through the receptacle, including, for example, forcing a piston into a cylinder, use of gases having a high vapor pressure, expansion of a liquid to a gas, and the like. Various techniques for producing the high pressure gas stream are further described in, for example, U.S. Pat. No. 5,740,794, and copending U.S. patent application Ser. Nos. 09/004,558, 09/312,434, 60/136,518 and 60/141,793, previously incorporated herein by reference. Gases that may be used to produce the gas stream include air, $CO_2$, HFCs, CFCs, and the like.

One exemplary way to channel the exiting powder is by use of an extraction tube that is inserted into the cavity. This tube may have a sharpened edge to permit the extraction tube to penetrate the receptacle cavity. Further, a seal may be used to ensure that the gas that is introduced into the cavity exits only through the extraction tube. In a similar manner, an inlet tube may be used to introduce the high pressure gas into the receptacle cavity.

The pressurized gas may be introduced into the cavity at one or more locations, and may exit through one or more extraction tubes. These may be located at a variety of locations within the cavity. For example, the inlets and outlets may be formed in a top end of the receptacle. Alternatively, a hole may be formed in the bottom end of the receptacle, and the extraction tube inserted into the top end of the receptacle so that it is generally aligned with the hole. The high pressure gas stream may then be flowed through the bottom hole and into the extraction tube. As another example, the high pressure gas may be introduced at opposite ends of the cavity, with the extraction tube being located between the inlets. Alternatively, the inlet may be at one end, and the outlet at the other end. In another aspect, the inlet tube may be positioned at an angle relative to the extraction tube to create a swirling effect within the cavity, thus enhancing the scouring of powder from the sides of the cavity.

Hence, by directly introducing a gas at a high flow velocity into the cavity, a greater amount of powder may be extracted from the cavity, thereby increase the emitted dose. Further, the standard deviation of the emitted dose may be reduced. Such techniques also increase the effectiveness in removing the powder with receptacles that have been shipped or transported which tends to agglomerate the powder or to cause the powder to adhere to the sides of the cavity.

Figure 2:
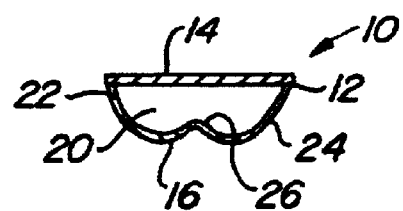
FIG. 2 is a cross sectional side view of the receptacle of FIG. 1, taken along lines 2—2.

Referring now to FIGS. 1 and 2, one embodiment of a receptacle 10 that may be used with the invention will be described. However, it will be appreciated that a wide variety of other receptacles may be used as previously described. Receptacle 10 comprises a receptacle body 12 having a top end 14 and a bottom end 16 (see FIG. 2). Conveniently, a tab 18 may be provided to facilitate handling of receptacle 10. Receptacle body 12 defines a cavity 20 into which a powder is sealed. Conveniently, receptacle body 12 may be constructed from essentially any type of material that is compatible with the powder held within cavity 20. Examples of materials that may be used include metals, such as aluminum, composites, plastics, and the like. One convenient way to construct receptacle 10 is to provide a thin strip of metal or composite and then pressing cavity 20 using a die. Another thin strip of metal may then be attached to the strip having the cavity to enclose and seal the cavity. Conveniently, ultrasonic welding, laser welding or heat sealings may be employed to adhere the two metal strips together. However, it will be appreciated that other techniques and materials may be employed to construct receptacle 10. Further, a number of receptacles may be formed as a single strip for multi-dose aerosolizers.

Cavity 20 has a generally circular or oval outer periphery 22 and is formed of a continuously curved wall 24 that may include a raised central region 26 at or near a center of the receptacle. In this way, a generally hemispherical or semi-toroidal interior is formed. Alternatively, the bottom may be substantially flat in geometry to facilitate its placement onto a holder.

Figure 3:
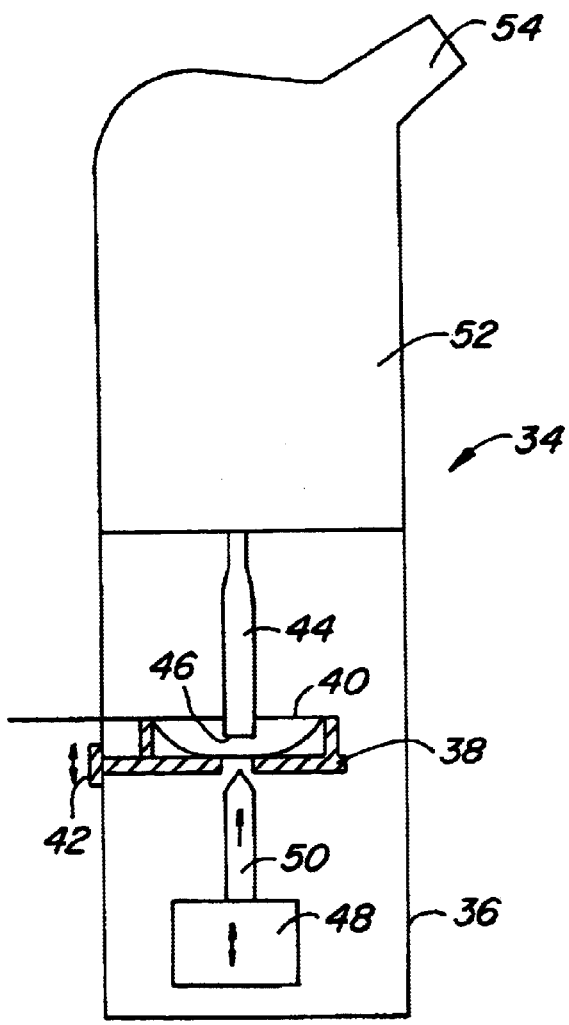
FIG. 3 is a schematic side view of an embodiment of an aerosolizing device according to the invention.

Shown schematically in FIG. 3 is an aerosolizing apparatus 34 that may be employed to aerosolize a powdered medicament. Apparatus 34 comprises a base 36 having a holder 38 for holding a receptacle 40. Holder 38 includes a knob 42 to permit receptacle 40 to be moved up and down as shown by the arrows. Also included within base 36 is an extraction tube 44 having a bottom end 46. By moving knob 42, extraction tube 44 may be inserted into receptacle 40 as shown. Alternatively, extraction tube 44 may be constructed to be movable so that it may be moved into receptacle 40.

Positioned below holder 38 is a pressure source 48 and an introduction tube 50. Pressure source 48 and/or introduction tube 50 may be moved vertically upward as illustrated by the arrows to pierce receptacle 40 and insert introduction tube 50 into or adjacent to receptacle 40. An amount of pressurized gas may then be released from pressure source 50 where it flows through the hole in the bottom end of receptacle 40 and into bottom end 46 of extraction tube 44. As one alternative, holder 42 may be lowered while pressure source 48 is kept stationary to form the hole in the bottom end of receptacle 40.

Positioned on base 36 is a capture chamber 52 having a mouthpiece 54. With such a configuration, receptacle 40 may be placed into holder 38 and extraction tube 44 inserted into receptacle 40. A hole may then be formed in the bottom end of receptacle 40 and a pressurized gas from pressure source 48 released to cause a high pressure gas stream to flow through extraction tube 44. In so doing, air flows through the cavity and into extraction tube 44 where the powder is aerosolized and ejected into capture chamber 52. Because the powder in receptacle 40 was initially sealed, gases may only enter through the hole in the bottom end and may only exit through extraction tube 44.

Figure 4:
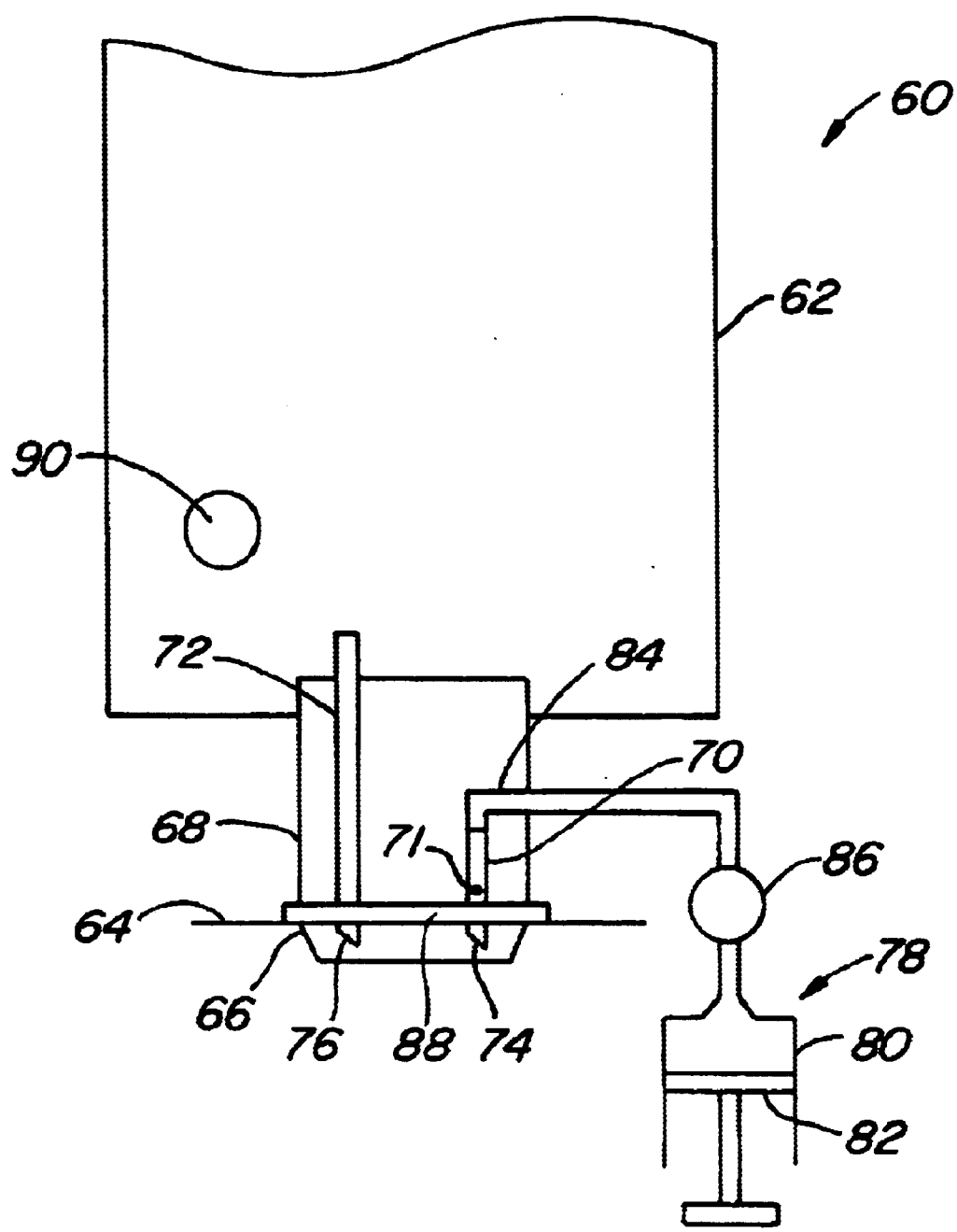
FIG. 4 is a schematic side view of another embodiment of an aerosolizing device according to the invention.
Figure 5:
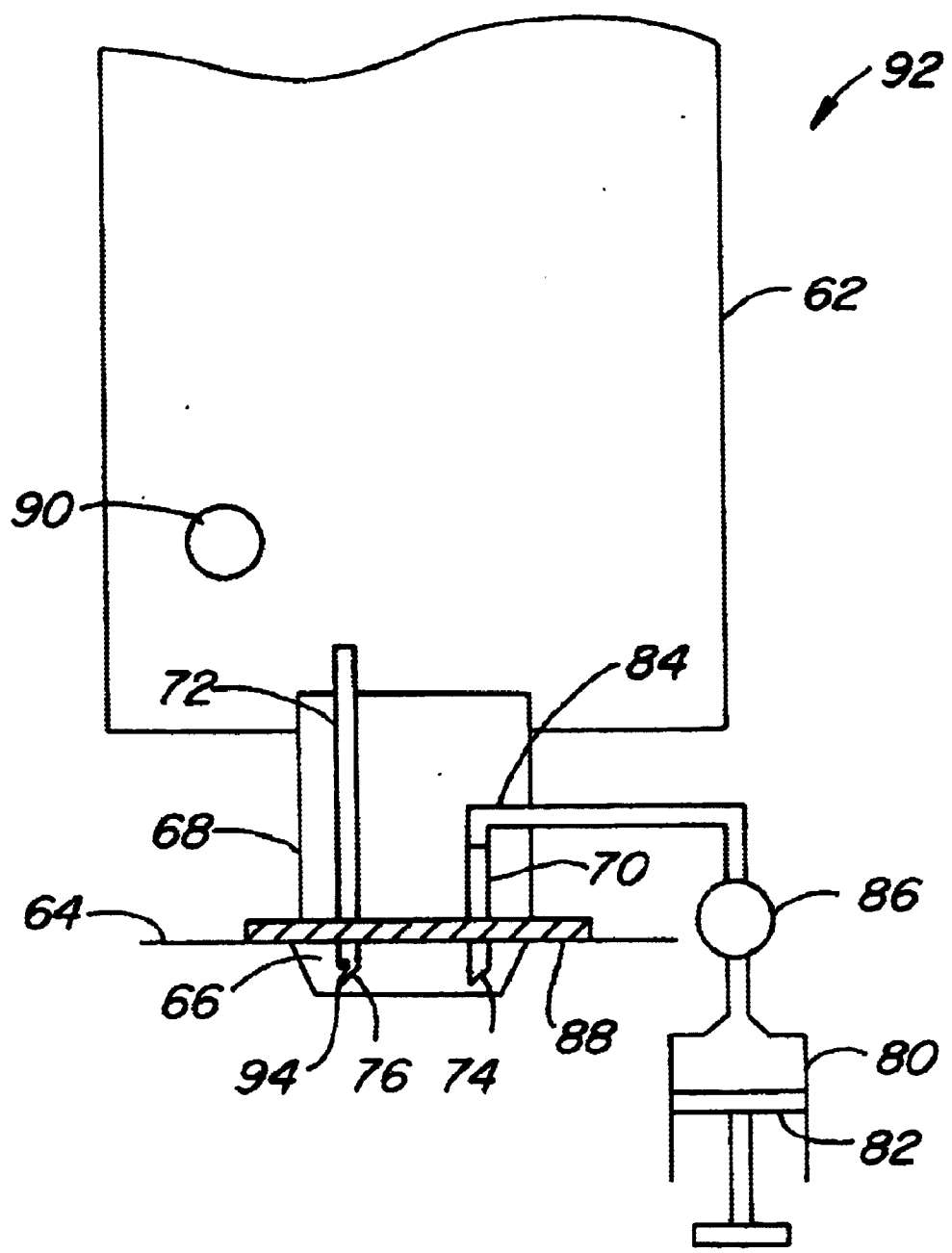
FIG. 5 is a schematic side view of still another embodiment of an aerosolizing device according to the invention.
Figure 6:
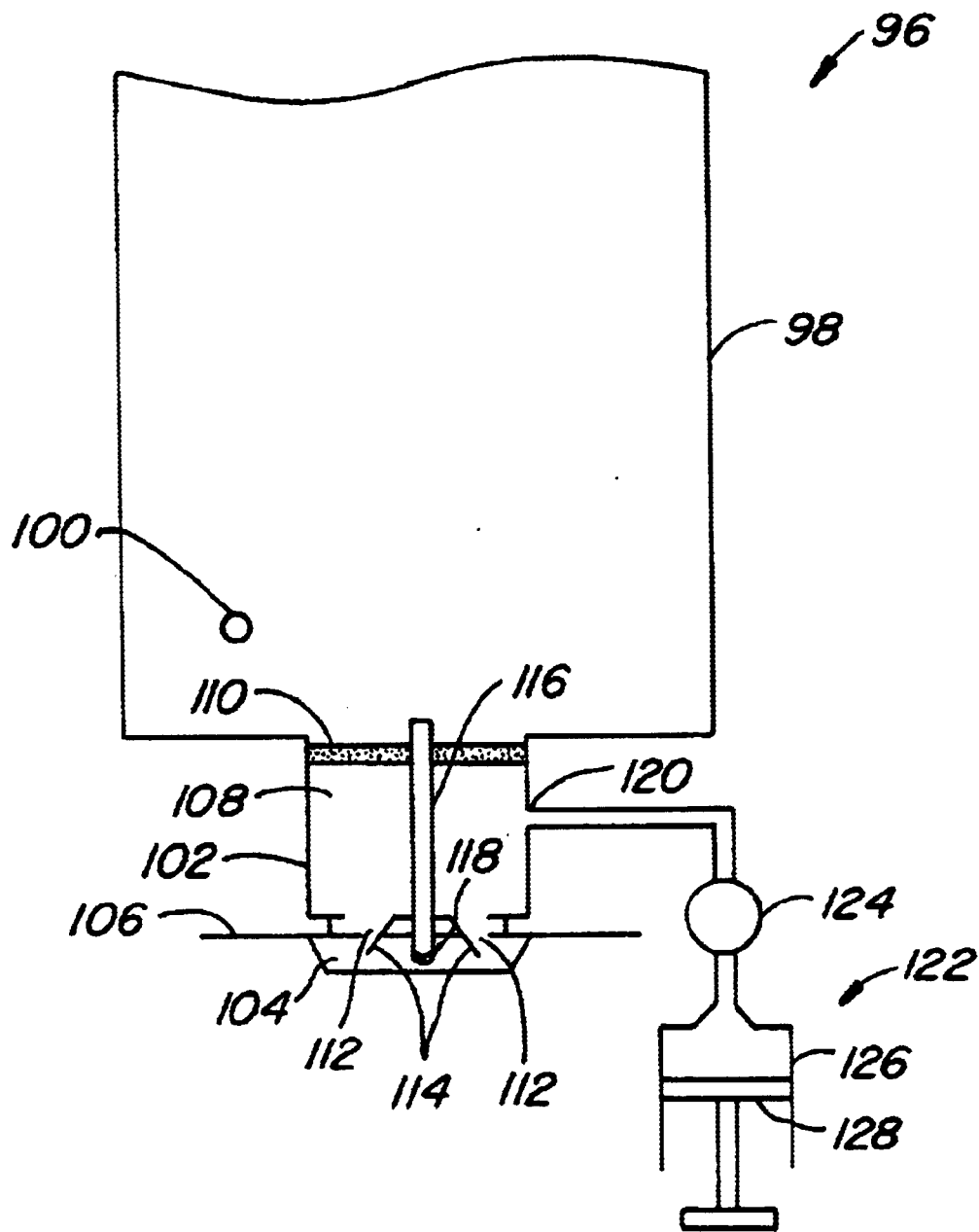
FIG. 6 is a schematic side view of yet another embodiment of an aerosolizing device according to the invention.

FIGS. 4–6 schematically illustrate other aerosolization apparatus that introduce a high velocity gas stream into a receptacle to remove and aerosolize the powder. Referring first to FIG. 4, an aerosolization apparatus 60 will be described. Apparatus 60 comprises a capture chamber 62 that is used to capture the aerosolized powder. Although not shown for convenience of illustration, capture chamber 62 is positioned on top of a housing which holds the various components of aerosolization apparatus 60. Such a housing is adapted to receive a receptacle 64 having a cavity 66 which holds a powder to be aerosolized. Apparatus 60 further includes a gas flow assembly 68 that is used to direct a high pressure gas into cavity 66 and to provide an exit path into capture chamber 62. More specifically, gas flow assembly 68 includes an inlet tube 70 to direct the high pressure gas into cavity 68 and an extraction tube 72 which permits the high pressure gas and entrained powder to exit into capture chamber 62. Conveniently, inlet tube 70 includes a sharpened end 74, and extraction tube 72 also includes a sharpened end 76. In this way, tubes 70 and 72 may pierce the top surface of receptacle 64 to gain access into cavity 66. To pierce the top surface, gas flow assembly 68 may be moved against receptacle 64 or vice versa. For example, receptacle 64 may be held within a movable carriage that forces receptacle 64 against ends 74 and 76 when the powder is ready to be aerosolized.

To supply the pressurized gas, aerosolization apparatus 60 further includes a pressure source 78 that comprises a cylinder 80 and a piston 82 that is slidable within cylinder 80. Connecting pressure source 78 to inlet tube 70 is a tube 84. Disposed between tube 84 and pressure source 78 is a valve 86. In operation, piston 82 is moved within cylinder 80 to provide a pressurized gas. When the user is ready to aerosolize the powder, valve 86 is opened to permit the high pressure gas to flow at a relatively high velocity into cavity 66. The high pressure gas stream has sufficient energy to deagglomerate the powder within cavity 66 as well as to scour any adhered powder from the sides of cavity 66. The powder is then forced by the high pressure gas stream into extraction tube 72 where it flows into capture chamber 62 and is available for aerosolization. The high shear rate inside the extraction tube further deagglomerates the powder. To prevent the high pressure gas from escaping through the openings created in receptacle 64, a seal 88, such as an epoxy or elastomer gasket, may be provided between gas flow assembly 68 and the top end of receptacle 64. The inlet tube 70 may also have a small hole 71 in it above the receptacle to pressurize the space above seal 88 and further reduce the likelihood of leaking some powder laden gas. In this way, gases may be input into cavity 66 only through inlet tube 70 and escape only through extraction tube 72.

To facilitate the removal of the aerosolized powder from capture chamber 62, a vent 90 may be provided in capture chamber 62. Alternatively, an alternative flow path may be provided through gas flow assembly 68 to permit outside chase air to be drawn into capture chamber 62 upon inhalation by the user.

Conveniently, aerosolization apparatus 60 may be constructed to be compatible with many of the components used to construct the aerosolization devices described in U.S. Pat. Nos. 5,458,135, 5,775,320, 5,740,794, 5,785,049, and 6,089,228, and copending U.S. patent application Ser. No. 09/312,434, filed Jun. 4, 1999, Ser. No. 60/136,518, filed May 28, 1999, Ser. No. 60/141,793, filed Jun. 30, 1999, and Ser. No. 09/583,312, file May 30, 2000, previously incorporated by reference. For example, gas flow assembly 68 may conveniently be interchanged with the multi-flow ejector devices described in these patents. Further, the pressure sources of the aerosolization devices described in these patents may alternatively be used as pressure source 78 of aerosolization apparatus 60.

Although not shown, it will further be appreciated that aerosolization apparatus 60 may include various other components to facilitate operation. For example, a handle may be employed to move piston 82 within cylinder 80 in a manner similar to that described in connection with U.S. Pat. Nos. 5,740,794 and 6,089,220 and copending U.S. patent application Ser. No. 09/312,434. Further, a fire button may be used to open valve 86 after the gas has been pressurized. Also, a mouthpiece may be coupled to capture chamber 62 to facilitate extraction of the aerosolized powder from capture chamber 62. Other features such as keyed receptacles, removable/disposal components, and the like may also be used.

Referring now to FIG. 5, another embodiment of an aerosolization apparatus 92 will be described. Apparatus 92 is similar to apparatus 60 and, for convenience of discussion, is labeled with the same reference numerals having identical components. With apparatus 92, the tip of extraction tube 72 is cut at an angle of approximately 30 to 45 degrees and includes a notch 94 just above end 76. Tube 72 cuts a flap in the top of cavity 66 during insertion. The notch 94 permits free flow into tube 72 so that pressure in the cavity does not force the flap against the tube opening in end 76 and impede flow.

Referring now to FIG. 6, an aerosolization apparatus 96 will be described. Apparatus 96 includes a capture chamber 98 that is coupled to a housing (not shown). Capture chamber 98 may optionally include a vent or flap valve 100 to permit chase air to enter into capture chamber 98 when the aerosolized powder is extracted in a manner similar to that previously described in other embodiments.

Apparatus 96 further includes a gas flow assembly 102 that is employed to direct a high pressure gas into a cavity 104 of a receptacle 106 and to direct the gas stream with the entrained powder into capture chamber 98. Gas flow assembly 102 includes a generally open interior 108 that is defined by the sides of assembly 102 and a cover 110. Gas flow assembly 102 includes a pair of inlet openings 112 to permit a high pressure gas to be introduced into cavity 104. Conveniently, a pair of piercing elements 114 are provided on gas flow assembly 102 to pierce the top end of receptacle 106 to provide access to cavity 104. This may be accomplished by forcing gas flow assembly 102 against receptacle 106 or vice versa.

When receptacle 106 is coupled to gas flow assembly 102, flow paths are provided into cavity 104. Gas flow assembly 102 further includes an extraction tube 116 to permit the gas stream with the entrained powder to be directed into capture chamber 98. Conveniently, extraction tube 116 may include a sharpened end 118 that also pierces receptacle 108 to gain access into cavity 104. Such a design is similar to the multi-flow ejector described in U.S. Pat. No. 6,089,228, previously incorporated by reference.

Coupled to gas flow assembly 102 is an inlet tube 120 which in turn is coupled to a high pressure gas source 122 via a valve 124. Gas source 122 comprises a cylinder 126 and a piston 128 that is slidable within the cylinder.

In operation, receptacle 106 is inserted into the housing and piercing elements 114 and sharpened end 118 are inserted into cavity 104. Piston 128 is moved within cylinder 126 to pressurize the gas. Valve 124 may then be operated to release the high pressure gas where it flows with a high velocity into interior 108. From interior 108, the high velocity gas flows through inlet openings 112 into cavity 104. The high velocity gas stream deagglomerates the powder and causes the sides of receptacle cavity 104 to be scoured of powder. The powder is then directed by the gas stream into extraction tube 116 where it enters into capture chamber 98. The patient may then inhale from a mouthpiece to transfer the aerosolized powder to the lungs.

As with other embodiments, the various components of aerosolization apparatus 96 may be included within the aerosolization devices described in U.S. Pat. Nos. 5,458, 135, 5,775,320, 5,740,794, 5,785,049, 6,089,228, and copending U.S. patent application Ser. No. 09/312,434, filed Jun. 4, 1999, Ser. No. 60/136,518, filed May 28, 1999, Ser. No. 60/141,793, filed Jun. 30, 1999, and Ser. No. 09/583, 312, file May 30, 2000. Further, many of the features described in these patents may also be incorporated into aerosolization apparatus 96 as previously described.

The invention has now been described in detail for purposed of clarity of understanding. However, it will be appreciated that certain changes and modifications may be practiced within the scope of the appended claims.

What is claimed is:

1. A method for aerosolizing a powder, the method comprising:

providing a receptacle having a cavity containing a powder;

inserting an access end of an extraction tube into the cavity;

forming an inlet opening in the receptacle; and flowing a pressurized gas through the inlet opening, through the cavity and through the extraction tube to move the powder in the cavity into the extraction tube where the powder is entrained in the gas to form an aerosol.

2. A method as in claim 1, further comprising producing a seal between the receptacle and the extraction tube so that substantially all of the pressurized gas exits through the extraction tube.

3. A method as in claim 2, further comprising permitting gases to enter the cavity only through the inlet opening.

4. A method as in claim 1, wherein the inlet opening forming step comprises piercing the receptacle with an access end of an inlet tube.

5. A method as in claim 4, further comprising flowing the pressurized gas through the inlet tube and into the cavity.

6. A method as in claim 1, wherein the pressurized gas is stored within a container, and further comprising releasing the pressurized gas from the container to permit the pressurized gas to flow through the inlet opening.

7. A method as in claim 6, wherein the container comprises a cylinder, and further comprising moving a piston within the cylinder to produce the pressurized gas.

8. A method as in claim 1, further comprising capturing the aerosol in a capture chamber.

9. A method as in claim 1, further comprising producing multiple inlet openings, and flowing the gas into the cavity through each inlet opening.

10. A method as in claim 1, further comprising inserting multiple outlet tubes into the cavity.

11. A method for aerosolizing a powder, the method comprising:
   providing a receptacle having a top end, a bottom end, and a cavity containing a powder;
   inserting a bottom end of an extraction tube into the cavity such that the bottom end of the extraction tube is spaced above the bottom end of the receptacle;
   forming a hole in the bottom end of the cavity; and
   flowing a pressurized gas through the hole in the bottom end of the receptacle, through the cavity and through the extraction tube to move the powder in the cavity into the extraction tube where the powder is entrained in the gas to form an aerosol.

12. A method as in claim 11, further comprising permitting gases to enter the cavity only through the inlet opening.

13. A method as in claim 11, wherein the bottom end of the receptacle includes a raised central region that extends upwardly into the cavity, and further comprising aligning the extraction tube with the raised central region such that the bottom end of the extraction tube is spaced apart from the raised central region.

14. A method as in claim 11, further comprising capturing the aerosolized powder in a capture chamber.

15. A method as in claim 11, further comprising releasing an amount of pressurized gas to produce the gas stream.

16. An apparatus for aerosolizing a powdered medicament, the apparatus comprising:
   a housing that is adapted to receive a receptacle having a cavity that holds a powder;
   a hole forming mechanism that is adapted to form an inlet hole in the receptacle;
   at least one extraction tube that is adapted to be placed into the cavity; and
   a pressure source that is adapted to provide a pressurized gas into the cavity through the inlet hole to permit the pressurized gas to flow through the cavity and through the extraction tube to move the powder in the cavity into the extraction tube where the powder is entrained in the gas to form an aerosol.

17. An apparatus as in claim 16, wherein the hole forming mechanism comprises at least one inlet tube having an access end that is adapted to pierce the receptacle, and wherein the pressure source is coupled to the inlet tube.

18. An apparatus as in claim 16, further comprising a seal that is adapted to provide a seal between the receptacle and the inlet tube and the extraction tube.

19. An apparatus as in claim 16, wherein the pressure source comprises a cylinder, and a piston that is slidable within the cylinder, and further comprising a valve that is operable to release the pressurized gas from the cylinder.

20. An apparatus as in claim 16, wherein the extraction tube has an access end that is adapted to pierce the receptacle.

21. An apparatus as in claim 16, further comprising a capture chamber coupled to the housing that is adapted to receive the aerosol, wherein the capture chamber includes a mouthpiece to permit the aerosol to be inhaled.

22. An apparatus as in claim 21, wherein the capture chamber includes a vent to permit gases to enter into the capture chamber as the aerosol is inhaled.

23. An apparatus for aerosolizing a powdered medicament, the apparatus comprising:
   a housing having a holder that is adapted to receive a receptacle having a cavity that holds a powder;
   a piercing mechanism that is adapted to pierce a hole in a bottom end of the receptacle;
   an extraction tube that is adapted to be placed into the cavity so as to be spaced above the bottom end of the receptacle and to be aligned with the hole in the bottom end.

24. An apparatus as in claim 23, further comprising a pressure source that is adapted to produce a pressurized gas that is flowed through the hole in the bottom end of the receptacle, through the cavity and into the extraction tube to move the powder from the cavity and into the extraction tube where the powder is entrained in the gas to form an aerosol.

25. An apparatus as in claim 23, further comprising a mouthpiece coupled to the housing that is adapted to receive a patient's mouth.

26. A system for aerosolizing a powdered medicament, the system comprising:
   a receptacle having a sealed cavity that holds a powder;
   a housing that is adapted to receive the receptacle;
   a hole forming mechanism that is adapted to form an inlet hole in the receptacle;
   at least one extraction tube that is adapted to be placed into the cavity; and
   a pressure source that is adapted to provide a pressurized gas into the cavity through the inlet hole to permit the pressurized gas to flow through the cavity and through the extraction tube to move the powder in the cavity into the extraction tube where the powder is entrained in the gas to form an aerosol.

27. A system as in claim 26, further comprising a seal member that forms a seal between the extraction tube and the receptacle such that the pressurized gas may enter only through the inlet and exit only through the extraction tube.

28. A system as in claim 26, wherein the extraction tube has a tapered distal end and a side hole spaced above the distal end to permit gas flow into the extraction tube through the side hole in the event that the distal end is blocked by a flap extending from the receptacle.

* * * * *